United States Patent [19]

Weuthen et al.

[11] Patent Number: 5,612,467
[45] Date of Patent: Mar. 18, 1997

[54] PROCESS FOR THE PRODUCTION OF LIGHT-COLORED ALKYL OLIGOGLYCOSIDE PASTES

[75] Inventors: Manfred Weuthen, Solingen; Burkhard Beckedahl; Irmgard Hartel, both of Duesseldorf, Germany

[73] Assignee: Henkel Kommanditgesellschaft auf Aktien, Duesseldorf, Germany

[21] Appl. No.: 212,000

[22] PCT Filed: Oct. 12, 1992

[86] PCT No.: PCT/EP92/02343

§ 371 Date: Apr. 21, 1994

§ 102(e) Date: Apr. 21, 1994

[87] PCT Pub. No.: WO93/08203

PCT Pub. Date: Apr. 29, 1993

[30] Foreign Application Priority Data

Oct. 21, 1991 [DE] Germany ............ 41 34 707.2

[51] Int. Cl.⁶ .................... C07G 3/00; C07H 15/04; C07H 1/00
[52] U.S. Cl. ............ 536/18.6; 536/4.1; 536/18.5
[58] Field of Search ............ 536/4.1, 18.6, 536/18.5

[56] References Cited

U.S. PATENT DOCUMENTS 3,450,690  6/1969  Gibbons, et al. ............ 536/18.5
3,839,318  10/1974  Mansfield ............ 536/18.6

FOREIGN PATENT DOCUMENTS 0077167  4/1983  European Pat. Off. .
0102558  3/1984  European Pat. Off. .
0132046  1/1985  European Pat. Off. .
0165721  12/1985  European Pat. Off. .
0362671  4/1990  European Pat. Off. .
0415192  3/1991  European Pat. Off. .
9003977  4/1990  WIPO .

OTHER PUBLICATIONS

Paul J. Flory, Principles of Polymer Chemistry, Cornell University Press, Ithaca, New York, 1953, pp. 35 to 37.

Primary Examiner—Gary E. Hollinden
Assistant Examiner—Everett White
Attorney, Agent, or Firm—Wayne C. Jaeschke; John E. Drach; Henry E. Millson, Jr.

[57] ABSTRACT

Light-colored alkyl oligoglycoside pastes can be obtained by a process in which a) glycose is reacted with fatty alcohols in the presence of acidic catalysts at elevated temperature to a residual content of glycose of less than 0.1% by weight, based on the starting quantity of glycose, b) water of reaction released is continuously removed from the equilibrium, c) the reaction products are neutralized with a base, the molar ratio of hydrogen ions in the reaction mixture to added base being from 1:1 to 1:1.5, d) unreacted fatty alcohols is separated by distillation, e) the residue is subsequently processed by addition of water to a paste having a solids content of 30 to 70% by weight, based on the paste, the paste is alkalized and, optionally, bleached by methods known per se.

20 Claims, No Drawings

PROCESS FOR THE PRODUCTION OF LIGHT-COLORED ALKYL OLIGOGLYCOSIDE PASTES

This is a 371 of PCT/EP92/02343, filed Oct. 12, 1992.

BACKGROUND OF THE INVENTION

1. Field of the Invention

This invention relates to a process for the production of light-colored alkyl oligoglycoside pastes, in which glycoses and fatty alcohols are reacted at elevated temperature in the presence of an acidic catalyst, the water of reaction is continuously removed, the reaction product is neutralized, unreacted fatty alcohol is separated by distillation and the residue is made into a paste with water.

2. Statement of the Related Art

Surface-active alkyl oligoglycosides have long been known as raw materials for the production of detergents. They are normally produced by acid-catalyzed acetalization of sugars (glycoses), more particularly glucose, with fatty alcohols. To obtain high yields, the alcohol component is used in a considerable excess, the water of reaction released is continuously removed from the reaction equilibrium and the reaction is terminated when virtually all the glucose, i.e. at least 99% by weight, has reacted off. The acidic catalyst is then neutralized and the excess fatty alcohol is separated by distillation. U.S. Pat. Nos. 3,839,318, 3,450,690, EP 0 132 046 A1 and WO 90/03977 are cited as representative of the large number of prior-art processes.

A serious technical problem in the production of alkyl oligoglycosides lies in the fact that, after separation of the fatty alcohol, the reaction products show strong discoloration so that, for aesthetic reasons, they can only be used as detergent raw materials after preliminary bleaching.

According to EP 0 077 167, the color quality of surface-active alkyl oligoglycosides can be improved by using a typical acidic catalyst together with an acidic reducing agent from the group consisting of phosphorous acid, hypophosphorous acid, sulfurous acid, hyposulfurous acid, nitrous acid and/or hyponitrous acid or the corresponding salts in the production of the alkyl oligoglycosides.

According to the teaching of EP 0 102 558, light-colored $C_{3-5}$ alkyl glucosides are obtained by carrying out the production of the alkyl glucosides in the presence of an acidic catalyst and an at least equivalent quantity of an alkali metal salt of a boric acid, preferably sodium perborate.

Finally, according to EP 0 165 721, color-stable products can be obtained by treating an aqueous solution of a surface-active alkyl oligoglucoside first with an oxidizing agent, preferably a hydrogen peroxide solution, and then with a sulfur dioxide source, for example an aqueous solution of sodium bisulfite.

In addition, it is known from the prior art that, after separation of the fatty alcohol, light-colored alkyl oligoglycosides can be obtained if neutralization of the acidic catalyst is carried out with magnesium oxide used in an excess of 200 to 500 mol-% and preferably 400 mol-%, based on the hydrogen ions present in the reaction mixture. However, the difficulty here is that magnesium oxide is difficult to incorporate in the reaction mixture. This is a major disadvantage, particularly for continuous operation, because the neutralization with magnesium oxide involves an additional dispersion step.

Another way of avoiding the problem of dispersing magnesium oxide in the reaction mixture is to use an aqueous sodium hydroxide solution, optionally with addition of MgO, as the neutralization base. However, the use of alkali metal hydroxides leads to discolored products both where stoichiometric quantities and where overstoichio-metric quantities are used. In addition, serious foaming problems occur during distillation, necessitating additional technical measures and adding to the overall costs of the process. In addition, the resulting products can only be bleached with considerable difficulty, if at all, by conventional methods.

Finally, another problem affecting the economic production of alkyl oligoglycosides lies in the fact that the fatty alcohol accumulating during the distillation phase cannot readily be returned to the acetalization step. In view of a large number of impurities, the fatty alcohol has to be subjected instead to a reducing treatment with borohydrides because otherwise the alkyl oligoglycosides would be adversely affected both in regard to their color quality and in regard to their performance properties.

Accordingly, the problem addressed by the present invention was to provide an improved process for the production of light-colored alkyl oligoglycoside pastes which would be free from the above-mentioned disadvantages.

DESCRIPTION OF THE INVENTION

The present invention relates to a process for the production of light-colored alkyl oligoglycoside pastes which is characterized in that a) glycose is reacted with fatty alcohols in the presence of acidic catalysts at elevated temperature to a residual content of glycose of less than 0.1% by weight, based on the starting quantity of glycose, b) water of reaction released is continuously removed from the equilibrium, c) the reaction products are neutralized with a base, the molar ratio of hydrogen ions in the reaction mixture to added base being from 1:1 to 1:1.5, d) unreacted fatty alcohols is separated by distillation, e) the residue is subsequently processed by addition of water to a paste having a solids content of 30 to 70% by weight, based on the paste, the paste is alkalized and, optionally, bleached by methods known per se.

It has surprisingly been found that, by limiting the quantity of unreacted glycose in the reaction mixture to values of less than 0.1% by weight, it is possible significantly to reduce the quantity of base required for neutralization, so that alkyl oligoglycosides which are light-colored without bleaching are reliably obtained.

The invention is based on the observation that, under the distillation conditions, residues of glycose in the reaction mixture decompose inter alia into carboxylic acids which, in turn, give rise to the formation of unwanted polyglycose and dark-colored components. By reducing the residual glycose content as in the process according to the invention, the quantity of base can be limited to the level required solely for neutralizing the acidic catalyst. There is no need to use a significant excess of base to neutralize acidic degradation products of the glycose, so that the problems discussed in the foregoing do not arise. Accordingly, it is possible by the process according to the invention continuously to produce inter alia light-colored alkyl glycoside pastes of reduced polyglycose content using small quantities of magnesium oxide.

Another advantage of the process according to the invention is that both the fatty alcohol accumulating and the alkyl oligoglycosides are substantially free from unwanted degradation products of the glycose and alkyl oligoglycosides. Accordingly, the fatty alcohol need only be subjected to a reducing aftertreatment at intervals of a few reaction cycles.

Finally, clear or only slightly clouded, dilute aqueous solutions can be produced with the alkyl oligo-glycosides obtained by the process according to the invention whereas the products according to the prior art are often clouded.

Glycoses which may be used as starting materials for the production of alkyl oligoglycoside by the process according to the invention are understood to be aldoses or even ketoses in the broadest sense. Typical examples are glucose, fructose, mannose, galactose, talose, gulose, allose, altrose, idose, arabinose, xylose, lyxose and ribose. The aldoses are preferably used by virtue of their better reactivity. Of the aldoses, glucose is particularly suitable by virtue of its ready accessibility and availability in commercial quantities. Accordingly, the alkyl oligoglycosides preferably produced by the process according to the invention are alkyl oligoglucosides.

Commercially available glucose generally contains 1 mol water of crystallization. This glucose containing water of crystallization may readily be used. In this case, however, it has proved to be useful additionally to remove the water of crystallization from the reaction medium by thermal measures before the glucose is contacted with the catatalyst. However, since anhydrous glucose is also commercially available in large quantities, it is preferably used in the form of a fine-particle powder.

Suitable acidic catalysts are, generally, any acidic compounds, including so-called Lewis acids, which catalyze the acetalization reaction between the fatty alcohol and the sugar molecule. Among these catalysts, sulfuric acid, phosphoric acid, aliphatic and/or aromatic sulfonic acids and sulfoacidic ion exchanger resins are particularly suitable. Particularly preferred catalysts for the process according to the invention are p-toluene sulfonic acid and/ or sulfosuccinic acid which have only a slight corrosive effect on equipment and pipes made of steel. Acidic ion exchanger resins are also suitable in the present case if the catalyst is to be separated off after acetalization of the glycose.

The acidic catalysts may be used in concentrations of 0.1 to 5% by weight and preferably in concentrations of 0.3 to 2% by weight, based on the fatty alcohol.

Suitable fatty alcohols are primary alcohols corresponding to formula (I)

$$R^1OH \qquad (I)$$

in which $R^1$ is an aliphatic, linear or branched hydrocarbon radical containing 6 to 22 carbon atoms and 0, 1, 2 or 3 double bonds.

Typical examples of such primary alcohols are caproic alcohol, caprylic alcohol, capric alcohol, lauryl alcohol, myristyl alcohol, cetyl alcohol, palmitoleyl alcohol, stearyl alcohol, oleyl alcohol, elaidyl alcohol, petroselinyl alcohol, linolyl alcohol, linolenyl alcohol, arachyl alcohol, gadoleyl alcohol, behenyl alcohol and erucyl alcohol. Saturated fatty alcohols containing 12 to 18 carbon atoms are preferred, those containing 12 to 14 carbon atoms being particularly preferred. As usual in oleochemistry, the fatty alcohols may also be present in the form of technical cuts of the type obtained, for example, in the high-pressure hydrogenation of fatty acid methyl esters based on natural fats and oils. Other suitable starting materials are oxoalcohols which may be obtained by ROELEN's oxo synthesis. Fatty alcohol mixtures based on coconut oil and beef tallow are preferred.

The conditions under which the three components glycose, catalyst and fatty alcohol are mixed may be varied within wide limits. Thus, in one variant of the process according to the invention, it is possible initially to introduce a mixture of the total quantities of all the components and to initiate the reaction by heating. In another variant, part of the fatty alcohol is initially introduced with the catalyst and a heated suspension of the glycose in the remainder of the alcohol is gradually added. In the case of laboratory mixtures, addition in portions is preferred whereas, in the case of industrial batches, continuous addition is preferred. The time intervals between addition of the portions are best selected so that a sub-stantially clear phase is continuously present, i.e. the quantity of unreacted glycose in the reaction mixture is kept small, i.e. no more than 10% by weight.

The mixing ratio of glycose to fatty alcohol may also be varied within wide limits. It is possible in this way to control the degree of distribution between alkyl monoglycoside and alkyl oligoglycosides in the reaction product. Glycose and fatty alcohol are normally used in a molar ratio of 1:1 to 1:10 and preferably in a molar ratio of 1:2 to 1:6.

In the case of laboratory batches and particularly in the case of industrial-scale batches, it has been found that the fine dispersion of the glycose in the fatty alcohol has a very positive effect on the quality of the reaction product. This fine dispersion is achieved by intensively mixing the finely powdered glycose, above all the glucose, optionally after fine grinding, with the fatty alcohol. For laboratory batches, it has proved to be suitable to use a typical high-speed laboratory stirrer or even an ultrasonic treatment for this purpose. In the case of industrial-scale batches, inline mixers, for example stator/rotor mixers, are preferably used for the fine dispersion. This fine dispersion measure has the desired secondary effect of heating the suspension.

A vacuum of about 10 to 50 mbar is applied during the formation and removal of the water of reaction. The mixture is heated and mixed, preferably continuously, during the reaction. Laboratory batches are heated and mixed simply by stirring whereas industrial-scale batches are heated and mixed by pumping through an external circuit incorporating a heat exchanger. When applying the heat required to maintain the reaction temperature, it is essential that only a small temperature difference is present between the wall of the reactor and the reaction mixture so that overheating is avoided. To establish this small temperature difference, it is sufficient with laboratory batches to use a standard oil bath with a thermostat and, at the same time, vigorously to stir the reaction mixture. With large-scale batches, it has proved to be particularly advantageous to apply the heat via an external circuit preferably consisting of a pump and a heat exchanger. To this end, part of the reaction mixture is continuously removed through a pipe, heated in the heat exchanger and returned to the reactor. It is possible in this way to avoid high reactor wall temperatures, i.e. above 125° C., and thus to prevent the color values of the end product from being adversely affected by the temperature control.

Where the portion variant of the process is applied, 30 to 70% by weight of the fatty alcohol is preferably initially introduced with the catalyst, the mixture is heated to 80° to 120° C. and the glycose is then added in the form of a suspension in the heated remainder of the alcohol, the glycose preferably being added continuously in a vacuum. The water of reaction formed is continuously distilled off. To determine the quantity of water of reaction, the water may be collected, for example, by freezing in a cold trap.

In another preferred embodiment of the process which starts out from the total quantity of mixture, the mixture of fatty alcohol and glycose is initially introduced and heated with stirring, i.e. to a sump temperature of around 80° C., and the acidic catalyst is subsequently added to the heated mixture. A vacuum is then applied, the temperature is increased to around 100° to 120° C. and the water of reaction formed is distilled off.

Accordingly, a temperature of 80° to 120° C. and, more particularly, 100° to 115° C. has proved to be optimal for the production of alkyl oligoglycosides.

Since, as already mentioned, the fatty alcohols can be used over a wide chain length range in the process according to the invention, the strength of the vacuum may also be adjusted so that the boiling point of the alcohol is lowered by at least 30° C. For the reaction of long-chain fatty alcohols containing 12 to 18 carbon atoms, the vacuum is preferably adjusted to a value of 10 to 50 mbar.

According to the teaching of the process according to the invention, it is essential for the production of light-colored alkyl oligoglycosides to limit the residual quantity of glycose in the reaction mixture. A necessary, but inadequate indication of quantitative reaction of the glycose is the end of the separation of water. The reaction is continued until the residual glycose content is less than 0.1% by weight and preferably less than 0.05% by weight. The glycose content may be determined by methods known per se, for example discontinuously by reaction with FEHLING's solution or continuously by flow injection analysis.

Suitable bases for neutralization of the catalyst are magnesium, calcium and/or zinc compounds. Typical examples are calcium hydroxide, calcium oxide, magnesium hydroxide, magnesium oxide, the zeolites NaA or NaX, preferably in combination with calcium hydroxide, basic magnesium carbonate, basic zinc carbonate, calcium carbonate, zinc oxide, magnesium methylate, magnesium ethylate, magnesium propylate or butylate, i.e. the alcoholates of low-boiling alcohols, preferably $C_{1-4}$ alcohols. It is particularly preferred to use magnesium oxide.

The quantity of base used is determined by the concentration of hydrogen ions in the solution. The molar ratio of hydrogen ions to base may be 1:1 to 1:1.5 and preferably 1:1.1 to 1:1.3.

The fatty alcohol is separated off by vacuum distillation. In general, falling-film evaporators and, in particular, thin-layer evaporators are particularly suitable for the careful separation of temperature-sensitive mixtures because extremely short residence times at the relatively high temperatures necessary can be achieved in apparatus such as these. Thin-layer evaporators are evaporators in which a highly viscous, high-boiling mixture is applied to a heated wall and is mechanically distributed thereon by rotating wiping elements. Thin liquid layers or liquid films are produced and the film surfaces are constantly renewed. The vapors formed flow in counter-current to the product film and pass from the evaporator into the externally arranged condenser.

To produce alkyl oligoglycosides containing less than 0.1% by weight residual fatty alcohol, based on the alkyl oligoglycoside, it has proved to be optimal to carry out the distillation process in a thin-layer evaporator at a sump temperature of 120° to 170° C. and under a reduced pressure of 0.01 to 1 bar and preferably 0.05 to 0.2 bar.

The alkyl oligoglycosides produced by the process according to the invention are mixtures which consist essentially of alkyl monoglycoside and the alkyl oligoglycosides essentially limited here to diglycosides and triglycosides—and small amounts of tetra—and pentaglyco-sides. The distribution between mono- and oligoglycosides in the process product gives a theoretical degree of oligomerization of 1 to 5. The process is preferably carried out so that the degree of oligomerization is between 1 and 1.5, the quantity of alkyl monoglycoside, based on the total quantity of alkyl monoglycoside and alkyl oligoglycoside, being well above 50% by weight. (For a definition of the degree of oligomerization, see Paul J. Flory, Principles of Polymer Chemistry, Cornell University Press, Ithaca, N.Y. 1953, pages 35 to 37). The total quantity of the other secondary constituents is generally below 10% by weight. The residual quantity of unreacted glycose is less than 0.1% by weight, based on the alkyl oligoglycoside. The percentage content of polymeric glucose in the end product is between 5 and 8% by weight, again based on the alkyl oligoglycoside.

The anhydrous alkyl oligoglucoside is processed with water to a paste having a solids content of 40 to 70% by weight. Both the anhydrous alkyl oligoglucosides and the pastes obtainable therefrom are light-colored. If desired, they may be bleached with an active oxygen compound, more particularly hydrogen peroxide, by methods known per se. The quantity of active oxygen compound used is generally 0.2 to 1.5% by weight, expressed as $H_2 O_2$ and based on the quantity of product after separation of the alcohol. Since the pH value falls during the bleaching step, a base, for example sodium hydroxide, is added together with the per compound to maintain a pH value in the range from 8 to 13.

For prolonged storage or prolonged transport of the paste-form reaction product, it can be important effectively to prevent microbial degradation processes. Accordingly, the paste-form reaction product produced in accordance with the invention best contains a standard antimicrobial agent in the usual quantity to improve stability in storage.

Finally, adequate stabilization of the paste against color deterioration and microbial degradation is achieved by adjusting the product to a pH value above 11.5 by addition of alkali hydroxides.

Industrial applications

The light-colored alkyl oligoglycoside pastes produced by the process according to the invention show excellent detergent properties and are suitable for use in laundry detergents, dishwashing detergents and cleaning preparations and also hair-care and body-care preparations in which they may be present in quantities of 0.1 to 25% by weight and preferably 1 to 10% by weight, based on the preparation as a whole.

The following Examples are intended to illustrate the invention without limiting it in any way.

EXAMPLES

Example 1

580 g (3 mol) $C_{12/14}$ coconut oil fatty alcohol (Lorol® Spezial, a product of Henkel KGaA, Dusseldorf/FRG; hydroxyl value 290) and 2.2 g (0.01 mol) p-toluenesulfonic acid corresponding to 0.4% by weight, based on the fatty alcohol —were introduced into a 2-liter three-necked flask equipped with an intensive stirrer and distillation column. The mixture was then heated to 110° to 114° C. and a suspension of 180 g (1 mol) anhydrous glucose (Puridex®, a product of Cerestar Deutschland GmbH) in another 580 g (3 mol) coconut oil fatty alcohol was added in portions in a vacuum of 10 to 15 mbar. The water of reaction was removed from the reaction equilibrium through the distillation column and was frozen and collected in a cold trap cooled with liquid nitrogen. A total of 18.2 g water was measured.

Towards the end of the reaction, the reaction mixture was stirred at 110° to 115° C., samples were taken at intervals of 15 minutes and the glucose content determined by FEHLING's method. The reaction was terminated at a residual glucose content of less than 0.1% by weight.

0.3 g (0.007 mol) magnesium oxide—corresponding to an excess of base of 30 mol-%, based on the hydrogen ions present in the solution—was then added to the cooled reaction mixture which, after stirring for 30 minutes, was transferred to a thin-layer distillation apparatus. 976 g coconut oil fatty alcohol were separated off with no foaming problems at a sump temperature of 120° to 170° C. and under a reduced pressure of 0.1 bar. The distillation residue, i.e. the actual product, accumulated in a quantity of 299 g. The characteristic data of the product are shown in Table 1. The anhydrous reaction product (hydroxyl value 656) was processed with water to a paste having a solids content of 50% by weight, based on the paste, and adjusted to pH 11.7 with aqueous sodium hydroxide solution. Comparison Example C1

The procedure was as described in Example 1, except that the reaction of the glucose with the coconut oil fatty alcohol was terminated at a residual glucose content of 0.95% by weight. 7.2 g of a 25% by weight sodium hydroxide solution—corresponding to an excess of 400 mol-%, based on the hydrogen ions present in the mixture—were then added to the product which, after stirring for 30 minutes, was transferred to a thin-layer distillation apparatus. 982 g coconut oil fatty alcohol were separated off with significant foaming at a sump temperature of 120° to 170° C. and under a reduced pressure of 0.1 bar. The distillation residue, i.e. the actual product, accumulated in a quantity of 302 g. The characteristic data of the product are set out in Table 1. The product was made into a paste as in Example 1.

Comparison Example C2

The procedure was as in Comparison Example C1, except that neutralization was carried out with 2.8 g (0.02 mol) magnesium oxide—corresponding to an excess of 400 mol-%, based on the hydrogen ions present in the mixture. 300 g alkyl oligoglycoside were obtained. The characteristic data of the product are set out in Table 1. The product was made into a paste as in Example 1.

TABLE 1

| | Composition of the reaction products Percentages in % by weight | | | | | | | |
|---|---|---|---|---|---|---|---|---|
| | Homolog distribution | | | | | | | |
| Example | MG % | DG % | TG % | HG % | FA % | PG % | CV Klett | Sln. |
| 1 | 68.7 | 15.9 | 5.0 | 3.2 | 0.7 | 6.5 | 70 | Clear |
| C1 | 69.7 | 15.5 | 4.9 | 2.1 | 0.8 | 7.0 | 400 | Clear |
| C2 | 69.0 | 15.4 | 5.0 | 2.8 | 0.7 | 7.1 | 400 | Cloudy |

Legend:
MG = monoglucoside
DG = diglucoside
TG = triglucoside
HG = higher glucosides
FA = fatty alcohol
PG = polyglucose
CV = Klett color value, 5% by weight aqueous solution, pH 7, 1 cm round cuvette, blue filter (400–465 nm)
Sln. = appearance of a 10% by weight aqueous solution, pH = 10

What is claimed is:

1. A process for the production of light colored alkyl oligoglycoside pastes comprising the steps of: (1) reacting a glycose and a fatty alcohol having from 6 to 22 carbon atoms in the presence of an acid catalyst at an elevated temperature not above 125° C. while continuously removing the water of reaction to form a reaction product which is comprised of unreacted fatty alcohol and less than about 0.1% by weight residual glycose based on the initial amount or said glycose; (2) neutralizing said reaction product with a base wherein the molar ratio of hydrogen ions in said reaction mixture to said base is from about 1:1 to about 1:1.5; (3) removing said unreacted fatty alcohol by distillation to form a residue; (4) adding water and aqueous sodium hydroxide to said residue to form a paste having a solids content of from about 30% to about 70% by weight and a pH of greater than 11.5.

2. The process of claim 1 wherein said glycose is glucose.

3. The process of claim 1 wherein said fatty alcohol is a compound of the formula (I)

$$R^1OH \qquad (I)$$

wherein $R^1$ is an aliphatic, linear or branched hydrocarbon radical having from 6 to 22 carbon atoms and from 0 to 3 double bonds.

4. The process of claim 1 wherein the mole ratio of glycose to fatty alcohol is from about 1:1 to about 1:10.

5. The process of claim 1 wherein said acid catalyst is p-toluenesulfonic acid, sulfosuccinic acid, or a combination thereof.

6. The process of claim 1 wherein the concentration of said acid catalyst is from about 0.1 to about 5.0% by weight of said fatty alcohol.

7. The process of claim 1 wherein step (1) is carried out at a temperature of from about 80° C. to about 120° C.

8. The process of claim 1 wherein said base in step (2) is a compound of magnesium, calcium, zinc or a combination thereof.

9. The process of claim 1 wherein the distillation of step (3) is carried out by a thin layer distillation at a temperature of from about 120° C. to about 170° C. and a pressure of from about 0.01 to about 1 bar.

10. The process of claim 9 wherein step (3) is carried out at a pressure of from about 0.05 to about 0.2 bar.

11. The process of claim 1 wherein the mole ratio of glycose to fatty alcohol is from about 1:2 to about 1:6.

12. The process of claim 1 wherein step (1) is carried out at a pressure of from about 10 to about 50 mbar.

13. The process of claim 1 wherein step (1) is carried out at a temperature of from about 100 to about 115° C.

14. The process of claim 1 wherein in step (4) the paste has a solids content of from about 40 to about 70% by weight.

15. The process of claim 1 wherein in step (1) the glycose is in the form of a fine dispersion.

16. The process of claim 1 wherein the base in step (2) is magnesium oxide.

17. The process of claim 1 wherein in step (2) the molar ratio of hydrogen ions to base is from about 1:1.1 to about 1:1.3.

18. The process of claim 1 wherein step (1) is carried out at a temperature of from about 80° C. to about 120° C. and at a pressure of from about 10 to about 50 mbar, and the mole ratio of glycose to fatty alcohol is from about 1:1 to about 1:10; and said base in step (2) is a compound of magnesium, calcium, zinc or a combination thereof.

19. The process of claim 18 wherein in step (1) the fatty alcohol is a compound of the formula (I)

$$R_1OH \qquad (I)$$

wherein $R^1$ is an aliphatic, linear or branched hydrocarbon radical having from 6 to 22 carbon atoms and from 0 to 3 double bonds.

20. The process of claim 19 wherein in step (1) the glycose is glucose and the mole ratio of glucose to fatty alcohol is from about 1:2 to about 1:6; and wherein the distillation of step (3) is carried out by a thin layer distillation at a temperature from about 120° C. to about 170° C. and a pressure of from about 0.01 to about 1 bar.

* * * * *